(12) United States Patent
Darley et al.

(10) Patent No.: US 8,885,837 B2
(45) Date of Patent: Nov. 11, 2014

(54) IMPLANTABLE MEDICAL DEVICE

(75) Inventors: Ian Darley, Cromer Heights (AU);
Slobodan Ilic, Chatswood (AU);
Desmond A. McCusker, Balmain (AU);
John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 1826 days.

(21) Appl. No.: 11/814,507

(22) PCT Filed: Jan. 27, 2006

(86) PCT No.: PCT/US2006/002794
§ 371 (c)(1),
(2), (4) Date: May 27, 2008

(87) PCT Pub. No.: WO2006/081361
PCT Pub. Date: Aug. 3, 2006

(65) Prior Publication Data
US 2009/0034769 A1    Feb. 5, 2009

Related U.S. Application Data

(60) Provisional application No. 60/646,988, filed on Jan. 27, 2005.

(51) Int. Cl.
| H04R 5/00 | (2006.01) |
|---|---|
| H04R 25/00 | (2006.01) |
| A61N 1/36 | (2006.01) |
| A61N 1/375 | (2006.01) |

(52) U.S. Cl.
CPC ............ *A61N 1/36032* (2013.01); *A61N 1/375* (2013.01); *A61N 1/3758* (2013.01)
USPC ........... 381/23.1; 381/304; 381/312; 381/328

(58) Field of Classification Search
USPC .............. 600/25; 607/57; 381/23.1, 312, 326, 381/328; 623/10, 11.11
See application file for complete search history.

(56) References Cited

U.S. PATENT DOCUMENTS

| 5,085,628 | A | * | 2/1992 | Engebretson et al. .......... 600/25 |
| 5,782,891 | A | | 7/1998 | Hassler et al. |

(Continued)

FOREIGN PATENT DOCUMENTS

| EP | 0 499 940 A1 | 8/1992 |
| EP | 0 831 674 A2 | 3/1998 |

(Continued)

OTHER PUBLICATIONS

International Search Report. PCT/US06/02794 mailed Feb. 27, 2007.

(Continued)

*Primary Examiner* — Marlon Fletcher
(74) *Attorney, Agent, or Firm* — K&L Gates LLP

(57) ABSTRACT

An implantable device having an impact side likely to receive forces applied to the device is disclosed, the device comprising: a hermetically-sealed container including, a chassis having secure thereto at least one functional component, a first shell hermetically connected to the chassis to form a hermetic enclosure in which the at least one functional component is located, at least on feedthrough disposed in one or more of either the chassis and the first shell, configured to permit at least one input/output line to infiltrate the hermetic enclosure; and a second shell connected to the container so as to be spaced from and adjacent to the container to define the impact side of the device and to form with the container a non-hermetic enclosure.

39 Claims, 6 Drawing Sheets

(56) References Cited

U.S. PATENT DOCUMENTS

| | | | |
|---|---|---|---|
| 5,814,095 A | 9/1998 | Muller et al. | |
| 6,093,144 A * | 7/2000 | Jaeger et al. | 600/25 |
| 6,123,660 A | 9/2000 | Leysieffer | |
| 7,204,799 B2 * | 4/2007 | Miller et al. | 600/25 |
| 8,515,540 B2 * | 8/2013 | Leigh et al. | 607/36 |
| 2002/0051550 A1 * | 5/2002 | Leysieffer | 381/322 |

FOREIGN PATENT DOCUMENTS

| | | |
|---|---|---|
| EP | 1 846 089 A2 | 10/2007 |
| JP | 2894842 B2 | 5/1999 |
| JP | 2002-331038 A | 11/2002 |
| JP | 2008-528191 A | 7/2008 |
| WO | WO 95/34342 A1 | 12/1995 |
| WO | 98/03035 | 1/1998 |
| WO | WO 2006/081361 A2 | 8/2006 |
| WO | WO 2006/081361 A3 | 4/2007 |

OTHER PUBLICATIONS

European Patent Application No. 06719594.1, Extended Search Report mailed on May 11, 2010, 6 Pages.

Japanese Patent Application No. 2007-553228, Office Action mailed on Jan. 12, 2011, 4 Pages. Including an English language translation.

International Application No. PCT/US2006/02794, International Preliminary Report on Patentability mailed on Jul. 31, 2007, 4 Pages.

International Application No. PCT/US2006/02794, Written Opinion mailed on Feb. 27, 2007, 3 Pages.

Official Communication for European Application 06 719 594.1 dated Nov. 30, 2011 (4 pages).

* cited by examiner

IMPLANTABLE MEDICAL DEVICE

CROSS-REFERENCE TO RELATED APPLICATIONS

This application is a national stage application under 35 USC §371(c) of PCT Application No. PCT/US2006/002794, entitled "Implantable Medical Device," filed Jan. 27, 2006, which claims the benefit under 35 USC 119(e) of U.S. Patent Application No. 60/646,988, entitled "Implant Housing" filed Jan. 27, 2005, which is hereby incorporated by reference herein.

BACKGROUND

1. Field of the Invention

The present invention relates generally to medical devices and, more specifically, to implantable medical devices.

2. Related Art

There are several types of medical devices that are designed to be temporarily or permanently implanted within a patient or recipient ("recipient" herein). Such medical devices perform one or more of a variety of therapeutic functions such as stimulate nerve or other tissue, monitor biological functions or physiological parameters, transfer materials between the exterior and interior of the recipient, perform functions previously performed by organs or other biological systems, to name a few. Typically, such implantable medical devices include several mechanical, electrical, electro-mechanical and/or electronic components ("functional components" herein) located within an implantable housing. Depending on the application and intended function, the implantable device may be implanted directly underneath the skin or deep within a recipient adjacent to or in an organ or bone of the recipient.

The ability of the implantable device to maintain a hermetic enclosure contributes to the success of an implanted medical device. A hermetic enclosure is required to prevent fluids and tissue from damaging the functional components of the implantable device. The hermetic enclosure is also needed to prevent the implant from causing any adverse interaction within the recipient. For example, a breakdown in the hermetic enclosure may result in pain, infection, or interfere with normal biological and physiological processes. Furthermore, a compromised hermetic enclosure may, for example, cause intermittent functioning and/or a complete malfunction of the implantable medical device. These and other adverse effects may require the removal of the device, or may cause a recipient to stop using the implantable device to avoid the above or other adverse effects. Further, the recipient may be subject to physical events which result in force being applied to the implanted device, causing damage to the hermetic enclosure or the functional components contained therein.

In addition, many implantable devices require the housings to have a relatively thin profile so that when implanted, the device has a limited impact on the recipient. However, conventional designs to improve the hereticity and impact resistance of the enclosure often favor a larger device. A larger implant device may create a necessity for a bone excavation to hold the implant in a desired location and orientation in the recipient. On the other hand, conventional implants having a thin profile often sacrifice impact resistance for size.

SUMMARY

In accordance with one aspect of the present invention, an implantable device having an impact side likely to receive forces applied to the device is disclosed, the device comprising: a hermetically-sealed container including, a chassis having secured thereto at least one functional component, a first shell hermetically connected to the chassis to form a hermetic enclosure in which the at least one functional component is located, at least one feedthrough disposed in one or more of either the chassis and the first shell, configured to permit at least one input/output line to infiltrate the hermetic enclosure; and a second shell connected to the container so as to be spaced from and adjacent to the container to define the impact side of the device and to form with the container a non-hermetic enclosure.

In accordance with another aspect of the present invention, an implantable device is disclosed comprising: a top shell having an impact surface and side walls extending generally orthogonally from the periphery thereof, a bottom shell having a second surface portions of which are generally parallel with portions of said impact surface of said top shell, and having side walls extending generally orthogonally from the periphery thereof and coupled to one or more of said side walls of said top shell to form a non-hermetic enclosure between said top and bottom shells; a chassis disposed within said non-hermetic enclosure and secured to said second shell to form a hermetic enclosure therewith; and at least one functional component and disposed in said hermetic enclosure.

In accordance with a further aspect of the present invention, a hearing prosthesis is disclosed, comprising: an implantable device having an impact side likely to receive forces applied to the device, the device comprising: a hermetically-sealed container comprising: a chassis having secured thereto at least one functional component; a first shell hermetically connected to said chassis to form a hermetic enclosure in which said at least one functional component is located, at least one feedthrough disposed in one of either said chassis and said first shell, configured to permit at least one input/output line to infiltrate said hermetic enclosure, and a second shell connected to said container so as to be spaced from and adjacent to said container so as to define said impact side of said device and to form with said container a non-hermetic enclosure.

BRIEF DESCRIPTION OF THE DRAWINGS

Embodiments of the present invention are described herein in conjunction with the accompanying drawings, in which.

DETAILED DESCRIPTION

Figure 1:
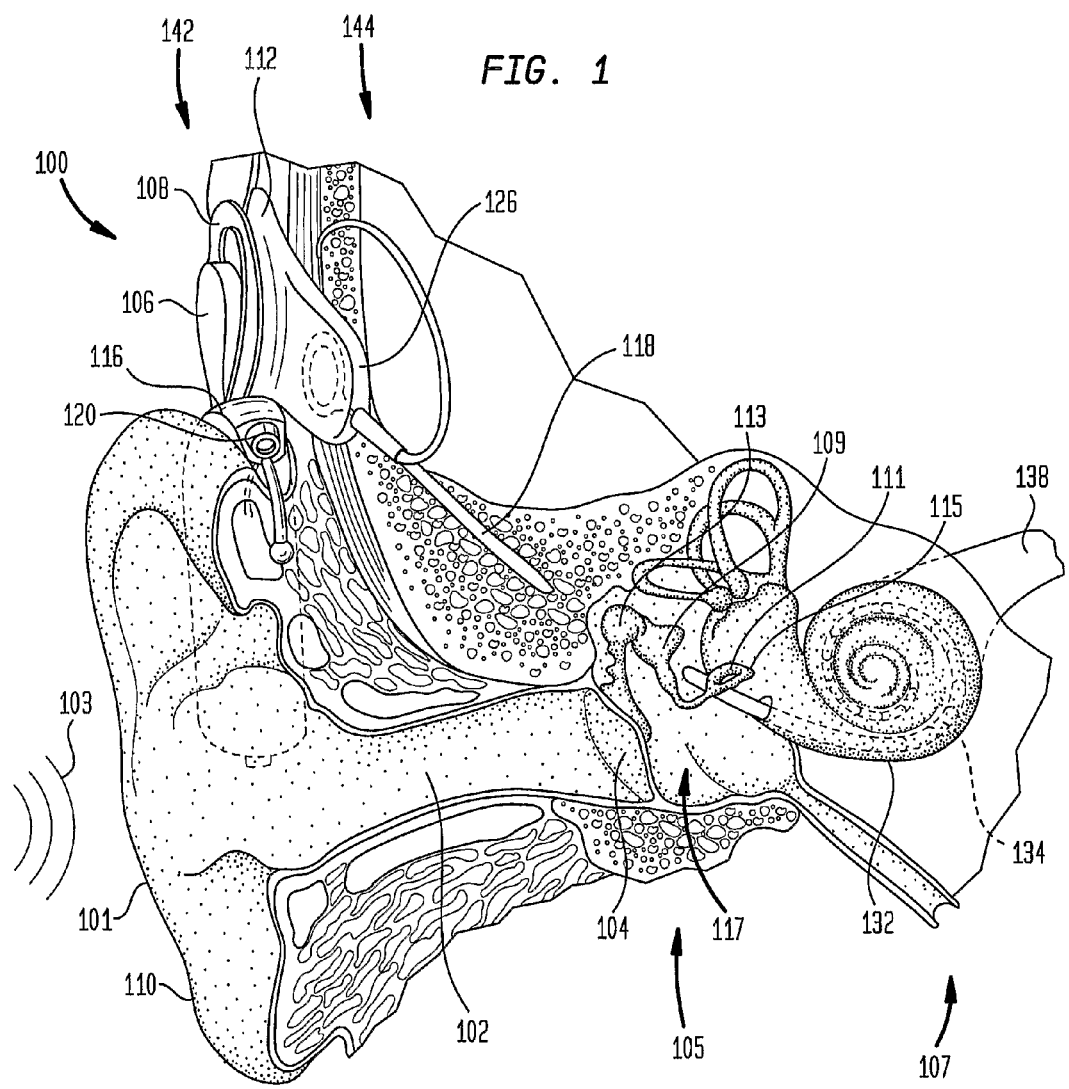
FIG. 1 is a schematic block diagram of one embodiment of an exemplary hearing prosthesis in which embodiments of the present invention may be advantageously implemented.

Aspects of the present invention are generally directed to an implantable device capable of having a desired minimal thickness without having to risk damage to or otherwise compromise the hermetic enclosure. The side of the implantable device that is more likely to receive external forces applied to the device due to the implant orientation and location of the device, referred to herein as the impact side, typically faces toward the skin of the implant recipient. The implant side of the device may receive significant external forces, particularly when the device is implanted close to or immediately beneath the skin. It follows, then, that an opposing side of the device is generally facing toward the interior of the recipient and, as such, is less likely to directly receive external forces applied to the device.

In certain embodiments disclosed herein, the device comprises a hermetically-sealed container comprised of a chassis having secured thereto at least one functional component, a bottom shell (also referred to as a first or lower shell herein) hermetically connected to the chassis to form a hermetic enclosure in which the functional component(s) is/are located. The container further comprises at least one hermetic feedthrough disposed in either, both, or a combination of the chassis and bottom shell. The feedthrough is configured to permit at least one input/output line to infiltrate the hermetic enclosure and, as such, not compromise the integrity of the hermetic enclosure. As used herein, the term "input/output line" refers to any wire, cable, tube, etc., that is utilized to transfer energy, data, materials, biological samples, etc. between the implantable device and the recipient, other implantable devices, external components, etc. A top shell (also referred to as a second or upper shell herein) is connected to the container so as to be spaced from and adjacent to the container to define the impact side of the implant device. The top shell and container form a non-hermetic enclosure having at least one aperture through which the input/output lines, if any, may be routed to connect the implantable device to other implanted or external systems, implantable devices including but not limited to electrodes, sensors, power supplies, etc.

Advantageously, the chassis and bottom shell may be designed to accommodate the functional components to achieve a desired minimal thickness, while the top shell may be designed to have a desired impact resistance. This is particularly beneficial in those implants which are implanted adjacent to bone immediately under the recipient's skin, such as the implantable components of a hearing prosthesis. Such devices are subject to the greatest external forces due to the lack of intermediate tissue and abutment to the mastoid bone. The minimal thickness of implant devices of the present invention may reduce or eliminate the extent to which the mastoid is excavated to accommodate the implantable device, while increasing the impact resistance of the device. In addition to the obvious benefits afforded recipients, surgeons have more flexibility in applying different surgical techniques and more options for securing the device itself.

Embodiments of the present invention are described herein primarily in connection with one type of stimulating medical device, a hearing prosthesis. Hearing prostheses include but are not limited to hearing aids, auditory brain stimulators, and COCHLEAR™ brand cochlear prostheses (commonly referred to as COCHLEAR™ brand cochlear prosthetic devices, COCHLEAR™ brand cochlear implants, COCHLEAR™ brand cochlear devices, and the like; simply, "cochlear implants" herein).

Cochlear implants use direct electrical stimulation of auditory nerve cells to bypass absent or defective hair cells that normally transduce acoustic vibrations into neural activity. Such devices generally use an electrode array inserted into the scala tympani of the cochlea so that the electrodes may differentially activate auditory neurons that normally encode differential pitches of sound. Auditory brain stimulators are used to treat a smaller number of recipients with bilateral degeneration of the auditory nerve. For such recipients, the auditory brain stimulator provides stimulation of the cochlear nucleus in the brainstem, typically with a planar electrode array; that is, an electrode array in which the electrode contacts are disposed on a two dimensional surface that can be positioned proximal to the brainstem.

FIG. 1 is a perspective view of an exemplary cochlear implant system in which embodiments of the present invention may be implemented. The relevant components of outer ear 101, middle ear 105 and inner ear 107 are described next below. An acoustic pressure or sound wave 103 is collected by outer ear 101 (e.g., the auricle) and channeled into and through ear canal 102. Disposed across the distal end of ear canal 102 is a tympanic membrane 104 which vibrates in response to acoustic wave 103. This vibration is coupled to oval window or fenestra ovalis 115 through three bones of middle ear 105, collectively referred to as the ossicles 117 and comprising the malleus 113, the incus 109 and the stapes 111. Bones 113, 109 and 111 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear implant 100 comprises external component assembly 142 which is directly or indirectly attached to the body of the recipient, and an internal component assembly 144 which is temporarily or permanently implanted in the recipient. External assembly 142 typically comprises one or more audio pickup devices (e.g., microphone(s)) 120 for detecting sound, a speech processing unit 116, a power source (not shown), and an external transmitter unit 106. External transmitter unit 106 comprises an external coil 108 and, preferably, a magnet (not shown) secured directly or indirectly to the external coil 108. Speech processing unit 116 processes the output of audio pickup device (e.g., microphone) 120 that is positioned, in the depicted embodiment, by ear 110 of the recipient. Speech processing unit 116 generates coded signals, referred to herein as a stimulation data signals, which are provided to external transmitter unit 106 via a cable (not shown). Speech processing unit 116 is, in this illustration, constructed and arranged so that it can fit behind outer ear 101 (e.g., the auricle). Alternative versions may be worn on the body or it may be possible to provide a fully implantable system which incorporates the speech processor and/or microphone into the internal component assembly 144.

Internal components 144 comprise an internal receiver unit 112, a stimulator unit 126 and an electrode assembly 118. Internal receiver unit 112 comprises an internal transcutaneous transfer coil (not shown), and preferably, a magnet (also not shown) fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes. Signals generated by stimulator unit 126 are applied by the electrodes of electrode array 134 to cochlear 32, thereby stimulating the auditory nerve 138.

In one embodiment, external coil 108 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 112 may be positioned in a recess of the temporal bone adjacent to ear 110 of the recipient.

Further details of the above and other exemplary prosthetic hearing implant systems in which embodiments of the present invention may be implemented include, but are not limited to, those systems described in U.S. Pat. Nos. 4,532,930, 6,537,200, 6,565,503, 6,575,894 and 6,697,674, which are hereby incorporated by reference herein in their entireties. For example, while cochlear implant 100 is described as having external components, in alternative embodiments, cochlear implant 100 may be a totally implantable prosthesis. In one exemplary implementation, for example, speech processing unit 116, including the microphone, speech processor and/or power supply may be implemented as one or more implantable components. In one particular embodiment, speech processing unit 116 may be contained within the hermetically sealed housing used for speech processing unit 116.

In one example, electrode array 134 may include a plurality of independent electrodes each of which may be independently stimulated. For example, in an embodiment, employing Cochlear's Nucleus 24 system, electrode array 134 includes 22 independent electrodes each of which stimulates a distinct area of the basilar membrane (not shown) of the recipient's cochlea 132. As one of ordinary skill in the art is aware, low-frequency sounds stimulate the basilar membrane most significantly at its apex, while higher frequencies more strongly stimulate the basilar membrane's base. Thus, electrodes of electrode array 134 located near the base of the cochlea are used to simulate high frequency sounds while electrodes near the apex are used to simulate low frequency sounds. Typically, in such a system, speech processing unit 116 stimulates only the electrodes with the largest signals. For example, cochlear implant 100 may estimate the outputs for each of the 22 electrodes and select the ones with the largest amplitude (that is, maxima). The number of maxima selected may vary, for example, between five (5) and ten (10), depending on a variety of factors. Moreover, the rate of stimulation, often referred to in units of pulses per second, may also vary. Each of the applied maxima will be referred to herein as a channel of stimulation (or stimulation channel). Thus, in an example in which eight (8) maxima are applied, the system will be described as applying eight (8) channels of stimulation.

As one of ordinary skill in the art will appreciate, the present invention may be used in combination with any speech strategy now or later developed, including but not limited to, Continuous Interleaved Sampling (CIS), Spectral PEAK Extraction (SPEAK), and Advanced Combination Encoders (ACE™). An example of such speech strategies is described in U.S. Pat. No. 5,271,397, the entire contents and disclosures of which is hereby incorporated by reference herein. The present invention may also be used with other speech coding strategies now or later developed. Certain embodiments of the present invention may be used on Cochlear Limited's Nucleus™ implant system that uses a range of coding strategies alternatives, including SPEAK, ACE™, and CIS. Among other things, these strategies offer a trade-off between temporal and spectral resolution of the coded audio signal by changing the number of frequency channels chosen in the signal path.

In the above exemplary application of cochlear implant 100, the implantable device is stimulator unit 126. It should be appreciated, however, that the implantable device may comprise other functional and operational components of cochlear implant 100 or other medical devices. For example, in the context of a cochlear implant, the implantable device may include other functional components that perform, for example, speech processing operations. Alternatively, the applicable cochlear implant may be a totally implantable system in which substantially all functional components requiring a hermetic enclosure would be included in the implantable device. To emphasize this, in the following description reference will be made to a implantable device rather than a specific component of a medical device, such as stimualtor unit 126 of cochlear prosthesis 100.

Figure 2A:
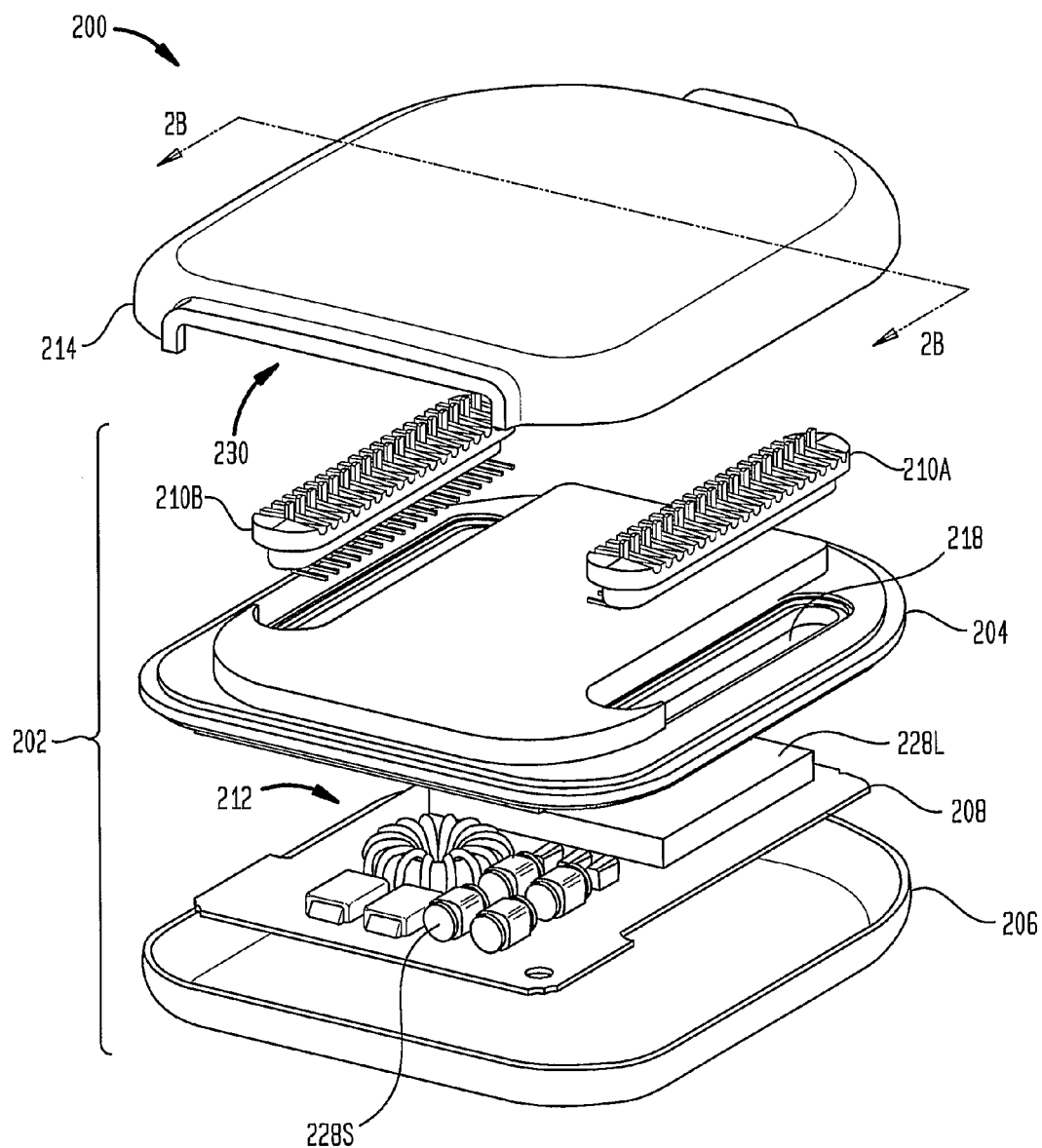
FIG. 2A is an exploded perspective view of an implant device in accordance with one embodiment of the present invention.
Figure 2B:
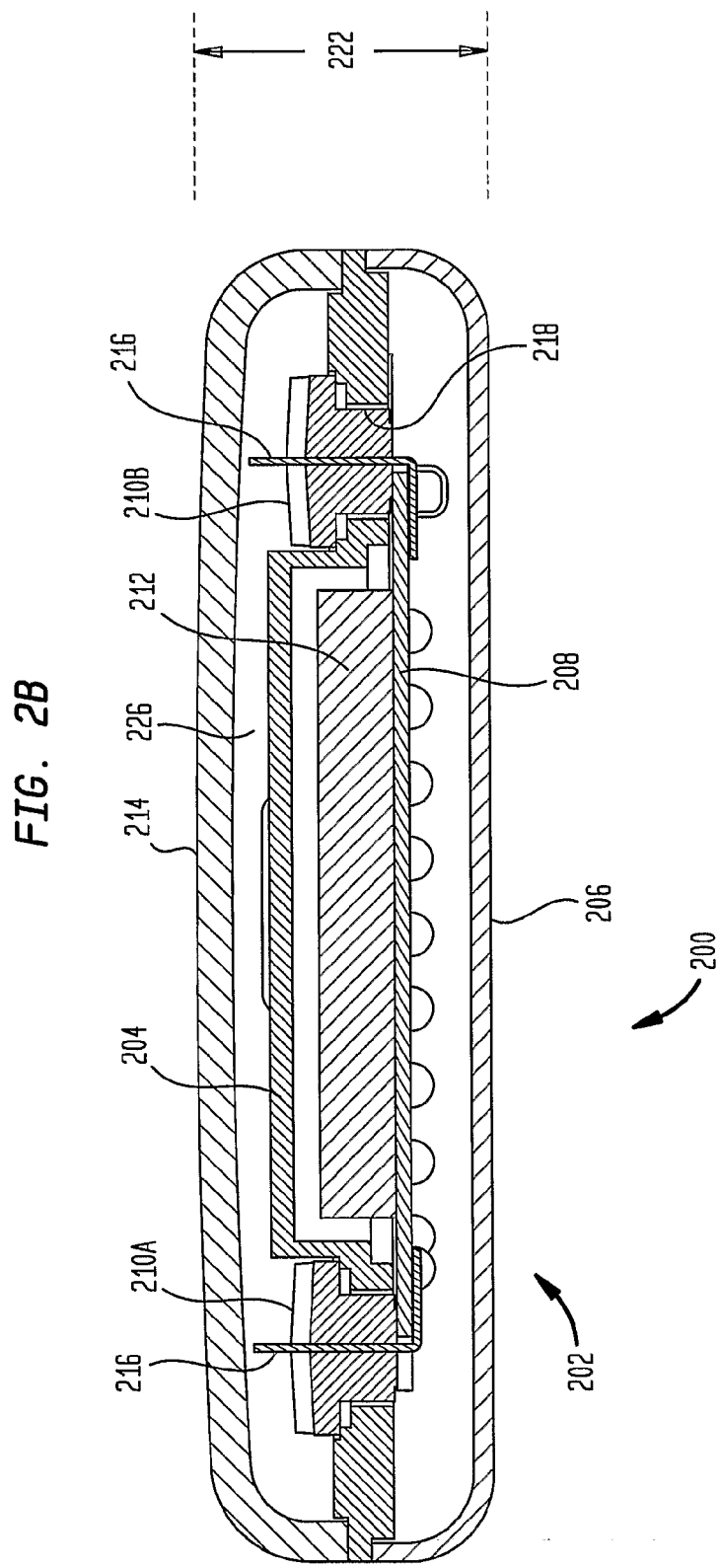
FIG. 2B is a cross-sectional view of the implant device illustrated in FIG. 2A taken along section line 2B-2B of FIG. 2A.
Figure 2C:
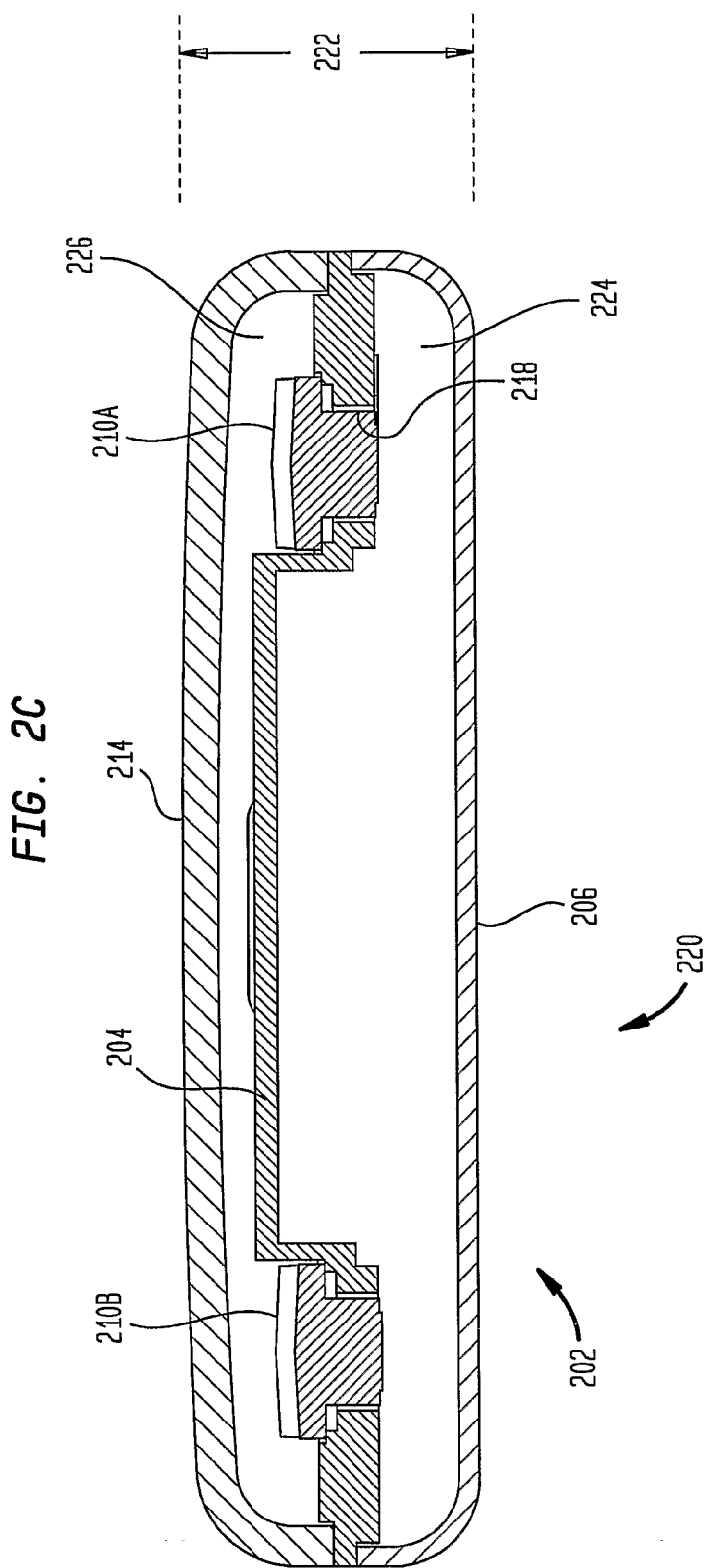
FIG. 2C is the same cross-sectional view of the implant device illustrated in FIG. 2B with the hermetic enclosure vacated of functional components.

FIG. 2A is an exploded perspective view of one embodiment of an implant device 200 in accordance with embodiments of the present invention. FIG. 2B is a cross-sectional view of the implant device illustrated in FIG. 2A taken along section line 2B-2B. FIG. 2C is the same cross-sectional view of the housing of the implant device illustrated in FIG. 2B; that is, the implant device with the hermetic enclosure vacated of functional components. Implantable device 200 is described next below with reference to FIGS. 2A-2C.

Implant device 200 comprises a hermetically-sealed container 202. Hermetically-sealed container 202 is formed by a bottom shell 206 hermetically connected to a chassis 204. As shown best in FIGS. 2B and 2C, container 202 defines a hermetic enclosure 224 in which functional components 212 are located. As noted, functional components include at least any components which are not to be exposed to biological systems, including mechanical, electrical, electro-mechanical and/or electronic components. In this exemplary application, functional components 212 include a printed wiring board 208 and electronic components 228 mounted on printed wiring board 208. In the embodiment illustrated in FIG. 2A, electronic components 228 may comprise one or more relatively large components 228L and one or more relatively small components 228S. As defined herein, relatively larger components 228L are those having a height which is, on average, generally greater than that of other components. Referring to FIG. 2B, the height of functional components 212 is the dimension of the component along an axis parallel with thickness 222 of implant device 200. Conversely, relatively smaller components 228S are those having a height which is generally less than that of other components 212. The allocation of components 228S and 228L in alternative embodiments of the present invention is described in detail below. Further, additional aspects and features of embodiments of chassis 204 are also described in detail below.

Container 202 further comprises at least one hermetic feedthrough 210 disposed in either chassis 204 and/or bottom shell 206. In the embodiment shown in FIGS. 2A-2C, two elongate hermetic feedthroughs 210A and 210B are disposed in apertures 218 of chassis 204. Such feedthroughs 210 are each configured to permit a input/output line 216 to infiltrate hermetic enclosure 224 without degrading the hermeticity of the enclosure. Input/output lines 216 may be, for example, wires (copper, fiber optic, etc.), cables, tubes, etc. that facilitate the transfer of energy, data, materials, biological samples, etc. between functional components 212 and the recipient, other implantable devices, external components, etc.

In the embodiment shown in FIG. 2B, one lead 216 extends from the bottom of printed wiring board 208 through one hermetic feedthrough 210A while another lead 216 extends from the bottom of printed wiring board 208 through the other hermetic feedthrough 210B. In the exemplary application described above with reference to FIG. 1, one such lead 216 is connected to an internal transcutaneous transfer coil and the other lead 216 is connected to electrode array 134. Hermetic feedthroughs 210 allow for many input/output lines of any type to infiltrate enclosure 224, without impairing or otherwise jeopardizing the hermeticity of enclosure 224.

Implantable device 200 has a side, referred to herein as the impact side, that is more likely to receive external forces applied to the device due to the implant orientation and location. That is, the surface of the implant device which faces toward the skin of the implant recipient is likely to receive external forces, particularly when the device is implanted close to or immediately beneath the skin. It follows, then, that an opposing side of the device is generally facing toward the interior of the recipient and, as such, is less likely to directly receive external forces which may be applied to the device.

A top shell 214 is connected to container 202 spaced from and adjacent to the container define the noted impact side of implant device 200. Top shell 214 and container 202 form a non-hermetic enclosure 226 best illustrated in FIGS. 2B and 2C. Enclosure 226 is non-hermetic due to the presences of at least one aperture 230 (FIG. 2A) through which input/output lines 216 are routed to connect to other implanted or external systems, devices, etc., as noted above.

Advantageously, top shell 214 may be designed to have a desired impact resistance while not requiring an increase in the size of container 202 nor resulting in a decrease in the hermeticity of enclosure 224. This is particularly beneficial in those implants which are implanted adjacent to bone immediately under a recipient's skin, such as stimulator unit 126 of hearing prosthesis 100. Such devices are subject to the greatest external forces due to their being implanted against the mastoid bone immediately beneath a recipient's scalp. The minimal thickness of implant devices of the present invention may reduce or eliminate the extent to which the mastoid is excavated to accommodate the implant, while increasing the impact resistance of the device.

Top shell 214 comprises a lateral surface defining the top surface of device 200, and side walls extending generally orthogonally from the lateral surface. Similarly, bottom shell 206 comprises a lateral surface defining the bottom surface of device 200, and side walls extending generally orthogonally from the lateral surface. As shown best in FIGS. 2B and 2C, top shell 214 and bottom shell 206 mate with opposing sides of a peripheral edge of chassis 204. It should be appreciated, however, that top and bottom shells 214, 206 may be coupled in a myriad of ways. In one alternative embodiment, for example, top and bottom shells 214, 206 directly mate with each other.

In the embodiments illustrated in FIGS. 2A-2C, the lateral surface of top shell 214 is slightly convex. Applied forces will be completely or partially absorbed by top shell 214 as well as transferred along top shell 214 to chassis 204 and bottom shell 206 and, ultimately, to the adjacent mastoid bone (not shown). Should implantable device 200 experience a large external force which causes it to flex inward, functional components 212 are also protected by chassis 204. In other words, there are two layers of material protecting functional components 212 from external forces, top shell 214 and chassis 204.

Top shell 214 may be designed to have a desired impact resistance. For example, in the embodiment illustrated in FIGS. 2B and 2C, top shell 214 has a thickness that is substantially greater than the thickness of bottom shell 206. Such an increase in thickness need not result in a increase in size of implant device 200. Rather, it may result in a decrease in the volume of non-hermetic enclosure 226. For example, in one embodiment, top layer 214 is formed from titanium having a thickness of between approximately 0.35 mm and 0.5 mm. In other embodiments, the thickness of top layer 214 is between approximately 0.40 mm and 0.45 mm. In the same or other embodiments, the thickness of top layer 214 is approximately double the thickness of bottom layer 206.

In some embodiments, an inner filler material may be injected or inserted in non-hermetic enclosure 226 and/or hermetic enclosure 224. The inner filler material may help the structural integrity of implantable device 200 by providing additionally impact resistance. Suitable inner filler materials include silicon, Santoprene™ or other impact-dampening materials that will be understood by those skilled in the art.

In one embodiment, implantable device 200 houses a printed circuit board 208 on which relatively larger electronic components 228L and small electronic components 228S are mounted. Relatively larger electronic components 228L are mounted towards the center of printed circuit board 208 while relatively smaller electronic components 228S are mounted on the perimeter of printed circuit board 208. As noted, the term relatively larger and smaller components refers to the height of the functional component, wherein the height is the distance along the axis which is orthogonal to the plane defined by printed circuit board 208. The height of functional components, then is parallel with the thickness 222 of implantable device 200.

Hermetic container 202 is configured such that a large volume of hermetic enclosure 224 is provided toward the center of implant device 200, providing sufficient space for functional components 212 having a relatively larger height. In the exemplary application of hearing prosthesis 100, for example, the large area may have a height of approximately 4 mm to 5 mm, and preferably 4.2 mm to 4.5 mm. The smaller areas are located on the perimeter of container 202, providing sufficient space to house functional components 228S having a relatively smaller height. In one embodiment, the smaller areas may have a height 222 of approximately 2 mm to 3 mm. In one embodiment, height 222 is approximately 2.4 mm to 2.6 mm and, preferably 2.5 mm. In some embodiments with multiple smaller areas, each smaller area may have substantially the same height to provide a substantially symmetrical container 202.

Figure 4:
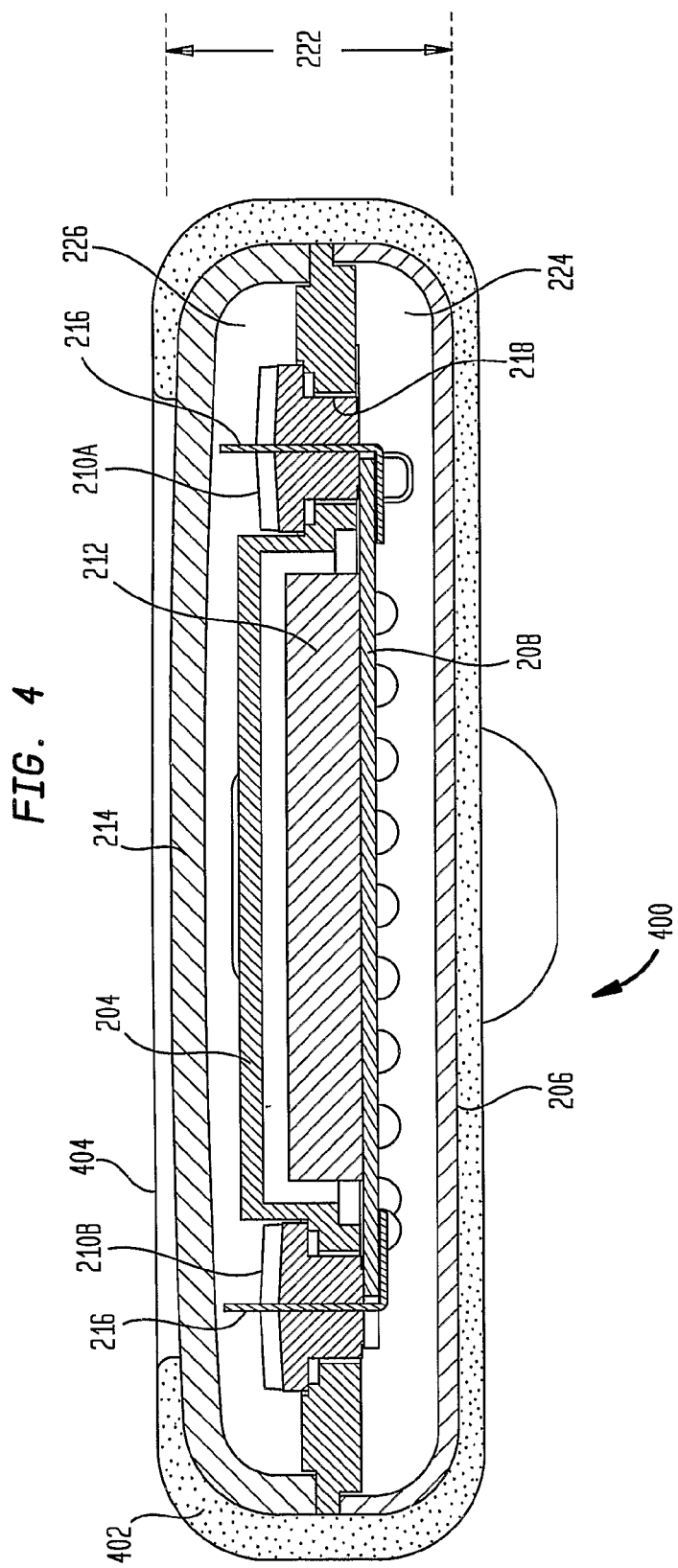
FIG. 4 is a cross-sectional view of an alternative embodiment of the implant device illustrated in FIG. 2A, taken along section lines 2B-2B in FIG. 2A.

In one embodiment of the present invention, implantable device 200 has an exterior surface that is substantially smooth surface; that is, there are no discrete changes in the surface tangent of implant device 200. One method for achieving the smoothness of the overall shape of implant device 200 is to use a silicone material designed to take advantage of the shape of top shell 214, as illustrated in FIG. 4. Top shell 214 may use a thicker layer of silicone in areas where better adhesion is desired. In one embodiment, the silicone shell may have a thickness of between about 0.2 mm to 0.25 mm.

Figure 3A:
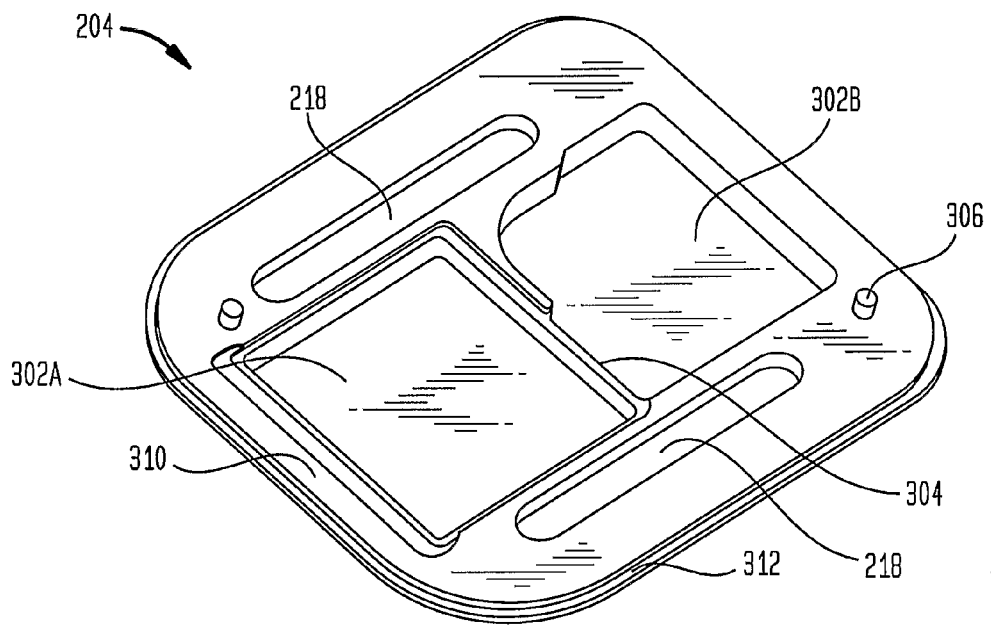
FIG. 3A is a bottom perspective view of a chassis constructed in accordance with an embodiment of the present invention.
Figure 3B:
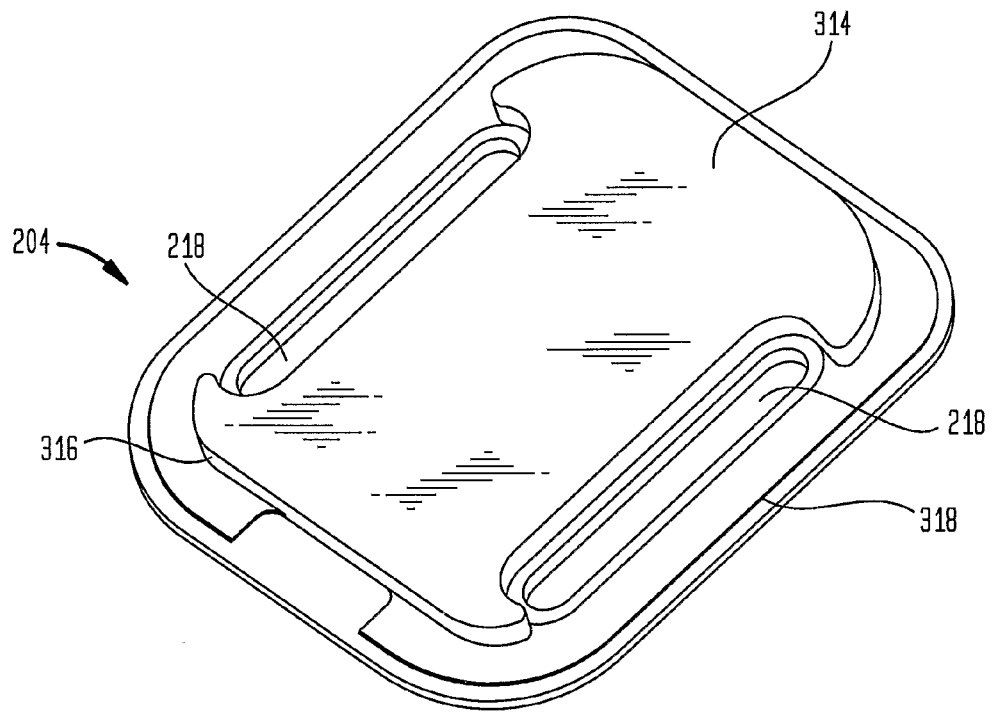
FIG. 3B is a top perspective view of the chassis illustrated in FIG. 3A.

FIGS. 3A and 3B show a top and bottom perspective view of one embodiment chassis 204. FIG. 3A shows two recesses 302 separated by web 304. Chassis 204 has pins 306 for aligning and/or positioning printed circuit board 208 on chassis 204. Feedthrough slots 218 are provided on brim 310 of chassis 204 so that feedthrough 210 may easily connect to printed circuit board when they are installed in the slots. A printed circuit board may rest against brim 310 so that the printed circuit board extends over feedthrough slots 218 and recesses 302. Chassis 204 has a lower sunken rim 312 around the edge of chassis 204 for mating with bottom shell 206 (not shown).

FIG. 3B is a top perspective view of chassis 204 illustrates a projection 314 created by recesses 302. Routing guides 316 are positioned so that coil and electrode wires (not shown) may extend into feedthrough slots 218 from external sources. Routing guides 316 dictate the geometry of the coil exit, which contributes to fatigue performance. Top shell 214 covers projection 314 and may mate with chassis 204 on upper sunken rim 318.

The features of a chassis used in the above and other embodiments of the present invention provide a number of benefits.

For example, one advantage of certain embodiments of the present invention is that the sunken rims 342, 318 provide an easy locating means for mating with the shells 214, 206 without the need for accurate jigging. Sunken rims 342, 318 also provide a shield against laser "shine through" which can damage internal components during mating of the shell to chassis by laser weld.

Feedthrough slots 218 of certain embodiments of the invention provide additional benefits as well. It is well known in the art that feedthroughs are generally tightly held to the electronic components and the printed circuit board within the chassis. If the size of chassis varies, the feedthrough slot size may also be varied. An automated production process may even measure individual feedthrough slots so that a matching chassis may be manufactured. Each feedthrough slot 218 may facilitate different feedthrough configurations which increases the flexibility of chassis 204.

In addition, chassis 204 positions and protects electronic components 228 in recesses 302. In the embodiment illustrated in the figures, chassis 204 has a recess 302A that partially surrounds and houses large electronic components 228L. Chassis 204 has a web 304 that separates recesses 302. Small electronic components 228S may be mounted on printed circuit board 204. Recesses 302B may also partially surround and house small electronic components 228S. Additional small electronic components 228S are mounted on the non-chassis side of printed circuit board 208, and are covered by a bottom shell layer 206. This minimizes the amount of space necessary in implant 200.

Top layer 214 may extend over chassis 202 and to create a curvature. Top layer 214 may be adhered to chassis 204 along an upper sunken rim 318, while bottom layer 206 may be adhered to chassis 204 along a lower sunken rim 312.

Chassis 204 may have a thickness of approximately 1.6 mm but may vary down to 0.25 mm in some areas. Suitable materials for chassis 204 include titanium or ceramic, among others.

The use of chassis 204 in implant device 200 provides manufacturing, space design and impact design advantages. Such advantages may be achieved by the presence of webs 304 in chassis 204. Webs 304 serve to define recesses 302A, 302B and which electronic components 228 will be compartmentalized with other components 228, if any. Also, when receiving an impact, a web 304 may contact printed circuit board 208 to divert the impact force from electronic components 228 to the printed circuit board 208.

A chassis may have any number of designs of recesses and webs and the design shown in FIGS. 3A and 3B is one example. For example, there may be three or more recesses, each having a different dimension. As noted, in some embodiments of the present invention, there may be an inner filler material in recesses 302 to protect components and to provide additional impact strength.

The chassis design of certain embodiments of the present invention protects delicate circuitry and larger electronic components. For example, a transformer is one of the larger components on the printed circuit board and may extend into a recess of the chassis. Also, to conserve space and to make the implant as thin as possible, embodiments of the present invention allow the transformer to sit "in" the chassis by extending through a recess, rather than rest solely within a recess. Another method to conserve space is to place the transformer within an opening of the printed circuit board, so that the transformer extends into a recess and through the printed circuit board and is covered by the bottom shell.

Other electronic components may be positioned within the implant depending on the need to protect the components from impact. For example, the integrated circuit (IC) is one of the most delicate parts of the implant, and one of the most critical in terms of functionality. In one chassis design of the present invention, the IC is mounted on the chassis side of the PCB, and the other components (including test points) on the other side. The IC may rest within a recess of the chassis for protection. Stress from impact may be redirected through the outer shell and/or to an inner filler, to the chassis and the web, and then through to the surrounding components, avoiding the IC. Recesses in the chassis may also house a chip insulator.

In certain embodiments of the present invention, the chassis is a complex part which locates and houses several other parts. Rather than having "complex" alignment tools or jigs, or having to locate parts by eye, this complexity is incorporated into the chassis. Producing a complex chassis may be done by many methods. Examples of such methods include milling, EDM, Wire EDM, coining and metal injection molding (MIM). The last two of these methods are relatively advantageous because the complexity is built into only one part (the die), rather than each part, as with milling. However, in milling, there exists the flexibility to match variations in size by changing the design by machining the complex chassis.

The complex chassis allows electronic components to be packed in a pre-designed layout within strict tolerances which are difficult to achieve by conventional methods. A complex chassis may increase reliability of implants by reducing the total number of parts, and lowering logistic costs while providing physical protection to electronic components. However, having a complex chassis requires additional time to manufacture the chassis depending on the method of manufacture. For example, machining may take more time to manufacture than chassis that is MIM or coined. One reason is that the complexity of the chassis is built into the die and chassis from the die may be produced in a very short time. Also a chassis that is MIM or coined may be produced through highly consistent and reliable manufacturing methods. Machining may include milling or selective laser melting (SLM) could also be used to chassis. Cycle time for SLM would be faster than milling but slower than MIM, which is slower again than coining. The cost of labor to perform each method of manufacture may also be an important consideration.

FIG. 4 is a cross-sectional view of an alternative embodiment of implant device 200. In this embodiment, a silicon layer 402 is adhered to the surface of implant device 200. The thickness of the silicone provides for a softer area that can be optionally used for screw fixation, as well as giving a soft feeling of the edges of the implant through the skin, due to the flexibility of top shell 214. Such an area may be used for securing a fixation plate (not shown) through a silicone boot. The fixation plate may be designed to fit the curvature of top shell 214. The fixation plate provides a means for securing a screw to a recipient's bone. It should be appreciated that any quantity of fixation plates or other fasteners and pins may be used to secure implant device 200 to the recipient.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An implantable device having an impact side likely to receive forces applied to the device, comprising:
    a hermetically-sealed container including:
        a chassis having secured to a side thereof corresponding to a major axis thereof at least one functional component;
        a first shell hermetically connected to said chassis to form a hermetic first enclosure, said at least one functional component not forming a part of the hermetic first enclosure rather being contained therein; and
        at least one feedthrough disposed in one or more of said chassis and said first shell, configured to permit at least one input/output line to infiltrate said hermetic first enclosure; and
    a second shell connected to said container so as to be spaced from and adjacent to said container to define said impact side of said device, said second shell and said container forming a second enclosure infiltrated by said at least one input/output line.

2. The implantable device of claim 1, wherein said second shell has at least one aperture at least partially defined by a surface of said second shell, wherein each said at least one aperture is configured to permit one or more of said at least one input/output line to extend from said implant device.

3. The implantable device of claim 1, wherein said at least one functional component comprises:
    a printed circuit board comprising a printed wiring board with electronic components mounted thereon.

4. The implantable device of claim 1, wherein said second second enclosure is a non-hermetic enclosure.

5. The implantable device of claim 1, wherein said plurality of functional components are positioned within said hermetic first enclosure such that functional components having relatively larger height are collocated in a central region of said hermetic first enclosure while functional components having relatively smaller height are located in one or more peripheral regions of said hermetic first enclosure.

6. The implantable device of claim 1, wherein said second shell is connected to said container such that impact forces applied to said second shell are transferred to said first shell.

7. The implantable device of claim 1, wherein said second shell is convex.

8. The implantable device of claim 1, wherein said second shell has a continuously curving exterior surface.

9. The implantable device of claim 1, wherein said first shell has a first thickness and said second shell has a second thickness different than said first thickness.

10. The implantable device of claim 1, wherein said device is a component of a prosthetic hearing implant, said at least one functional component comprises a plurality of functional components of a stimulator/receiver unit, said at least one input/output line comprises at least one cable configured to carry electronic signals between said implantable device and one or more of a transcutaneous coil and an electrode array.

11. The implantable device of claim 1, wherein the chassis comprises at least one recess each dimensioned to operationally receive one or more of said at least one functional component.

12. The implantable device of claim 1, wherein said first shell has a top wall and side walls extending from a periphery thereof, and wherein said second shell has a top wall and side walls extending from a periphery thereof, wherein one or more side walls of said first and second shells are configured to mate with one or more of said chassis and said first and second shell.

13. The implantable device of claim 12, wherein said chassis is configured with one or more sunken rims to mate as rabbet-joints with one or more of said sidewalls of said first and second shells, respectively.

14. The implantable device of claim 1, wherein said second shell is configured to at least partially absorb an impact force by flexing inward towards said container.

15. The implantable device of claim 1, wherein:
    said at least one functional component is disposed on a first side of said chassis; and
    said second shell is disposed on a second side of said chassis.

16. An implantable device comprising:
    a top shell having an impact surface and side walls extending generally orthogonally from the periphery thereof;
    a bottom shell having a second surface portions of which are generally parallel with portions of said impact surface of said top shell, and having side walls extending generally orthogonally from the periphery thereof to be coupled to with one or more of said side walls of said top shell to form a non-hermetic enclosure between said top and bottom shells;
    a chassis disposed within said non-hermetic enclosure and secured to said bottom shell to form a hermetic enclosure therewith; and
    at least one functional component secured to a side of said chassis corresponding to a major axis of said chassis, the at least one functional component not forming a part of said hermetic enclosure rather being contained therein,
    at least one feedthrough configured to permit at least one input/output line to infiltrate said hermetic enclosure and said non-hermetic enclosure.

17. The implantable device of claim 16, wherein said side walls of said top shell and said side walls of said bottom shell mate with opposing sides of said chassis.

18. The implantable device of claim 16, wherein said at least one functional component is secured to said chassis.

19. The implantable device of claim 16,
    wherein said at least one feedthrough is disposed in one or more of said bottom shell and said chassis.

20. The implantable device of claim 16, wherein said at least one functional component comprises a plurality of functional components of varying dimensions positioned within said hermetic enclosure such that functional components having a relatively larger height are collocated in a central region of said hermetic enclosure while functional components having a relatively smaller height are located in one or more peripheral regions of said hermetic enclosure.

21. The implantable device of claim 16, wherein said impact surface of said top shell is convex.

22. The implantable device of claim 16, wherein the chassis is comprises at least one recess each dimensioned to operationally receive one or more of said at least one functional component.

23. The implantable device of claim 17, wherein a rim of said chassis is configured with first and second sunken rims to mate as rabbet joints with said sidewalls of said top and bottom shells, respectively.

24. The implantable device of claim 16, wherein said top shell is configured to at least partially absorb an impact force by flexing inward towards said enclosure.

25. The implantable device of claim 16, wherein:
said at least one functional component is disposed on a first side of said chassis; and
said bottom shell is disposed on a second side of said chassis.

26. A hearing prosthesis comprising:
an implantable device having an impact side likely to receive forces applied to the device, the device comprising:
a hermetically-sealed container comprising:
a chassis having secured to a side thereof corresponding to a major axis thereof at least one functional component;
a first shell hermetically connected to said chassis to form a hermetic enclosure, said at least one functional component not forming a part of the hermetic enclosure rather being contained therein; and
at least one feedthrough disposed in one of either said chassis and said first shell, configured to permit at least one input/output line to infiltrate said hermetic enclosure; and
a second shell connected to said container so as to be spaced from and adjacent to said container so as to define said impact side of said device and to form with said container a non-hermetic enclosure infiltrated by said at least one input/output line.

27. The hearing prosthesis of claim 26, wherein said implantable device comprises a stimulator/receiver unit of said hearing prosthesis.

28. The hearing prosthesis of claim 26, wherein said implantable device comprises a speech processor of said hearing prosthesis.

29. The hearing prosthesis of claim 26, wherein said implantable device comprises substantially all functional components of said hearing prosthesis.

30. The hearing prosthesis of claim 26, wherein said second shell has at least one aperture at least partially defined by a surface of said second shell, wherein each said at least one aperture is configured to permit one or more of said at least one input/output line to extend from said implant device.

31. The hearing prosthesis of claim 26, wherein said at least one functional component comprises:
a printed circuit board comprising a printed wiring board with electronic components mounted thereon.

32. The hearing prosthesis of claim 26, wherein said at least one functional component comprises a plurality of functional components, some of which are positioned within said enclosure such that functional components having relatively larger height are collocated in a central region of said enclosure while functional components having relatively smaller height are located in one or more peripheral regions of said enclosure.

33. The hearing prosthesis of claim 26, wherein said second shell is coupled to said enclosure such that impact forces applied to said second shell are transferred to said first shell.

34. The hearing prosthesis of claim 26, wherein said second shell is convex.

35. The hearing prosthesis of claim 26, wherein said second shell has a continuously curving exterior surface.

36. The hearing prosthesis of claim 26, wherein the chassis comprises at least one recess each dimensioned to operationally receive one or more of said at least one functional component.

37. The hearing prosthesis of claim 26, wherein:
said first shell has a top wall and side walls extending from a periphery thereof;
said second shell has a top wall and side walls extending from a periphery thereof; and
said chassis is configured with first and second sunken rims to mate as rabbet joints with said sidewalls of said top and bottom shells, respectively.

38. The hearing prosthesis of claim 26, wherein said second shell is configured to at least partially absorb an impact force by flexing inward towards said container.

39. Hearing prosthesis of claim 26, wherein:
said at least one functional component is disposed on a first side of said chassis; and
said second shell is disposed on a second side of said chassis.

* * * * *